(12) United States Patent
Nakatsubo et al.

(10) Patent No.: US 8,962,521 B2
(45) Date of Patent: Feb. 24, 2015

(54) COATING FOR HUMIDITY INDICATOR, METHOD FOR PRODUCTION OF THE COATING, AND HUMIDITY INDICATOR USING THE COATING

(75) Inventors: Kunio Nakatsubo, Tokyo (JP); Tatsuya Ogawa, Tokyo (JP); Hitoshi Otomo, Tokyo (JP); Midori Fujisaki, Tokyo (JP)

(73) Assignee: Kyodo Printing Co., Ltd., Tokyo (JP)

( * ) Notice: Subject to any disclaimer, the term of this patent is extended or adjusted under 35 U.S.C. 154(b) by 1343 days.

(21) Appl. No.: 12/296,693

(22) PCT Filed: Apr. 25, 2007

(86) PCT No.: PCT/JP2007/058939
§ 371 (c)(1),
(2), (4) Date: Dec. 12, 2008

(87) PCT Pub. No.: WO2007/125953
PCT Pub. Date: Nov. 8, 2007

(65) Prior Publication Data
US 2009/0124497 A1    May 14, 2009

(30) Foreign Application Priority Data
Apr. 26, 2006   (JP) .................. 2006-122059

(51) Int. Cl.
*B41M 5/20* (2006.01)
*G01N 31/22* (2006.01)
*G01N 21/81* (2006.01)

(52) U.S. Cl.
CPC .............. *G01N 31/222* (2013.01); *G01N 21/81* (2013.01)
USPC .......................................... 503/209; 503/200

(58) Field of Classification Search
CPC .............................. G01N 31/222; G01N 21/81
USPC .................................................. 503/200, 209
See application file for complete search history.

(56) References Cited

U.S. PATENT DOCUMENTS

| | | | | |
|---|---|---|---|---|
| 3,622,533 | A | * | 11/1971 | O'Connor .................. 524/195 |
| 4,620,941 | A | * | 11/1986 | Yoshikawa et al. ........ 252/408.1 |
| 4,956,146 | A | | 9/1990 | Yuhki et al. |
| 5,290,704 | A | | 3/1994 | Chang |
| 2002/0001847 | A1 | * | 1/2002 | Elhard et al. .................... 436/39 |

FOREIGN PATENT DOCUMENTS

| | | |
|---|---|---|
| EP | 0333114 | 9/1989 |
| JP | 59-140097 | 8/1982 |
| JP | 58-216936 | 12/1982 |
| JP | 58-216936 | 12/1983 |
| JP | 60-78339 | 5/1984 |
| JP | 60-187860 | 9/1985 |
| JP | 63-17851 | 11/1988 |
| JP | 01-80841 | 3/1989 |
| JP | 1-201364 | 8/1989 |
| JP | 4-85374 | 3/1992 |
| JP | 4-239064 | 8/1992 |
| JP | 4-320950 | 11/1992 |
| JP | 5-34334 | 2/1993 |
| JP | 5-180825 | 7/1993 |
| JP | 5-296993 | 11/1993 |
| JP | 5-320616 | 12/1993 |
| JP | 6-289006 | 10/1994 |
| JP | 7-98279 | 4/1995 |
| JP | 7-98309 | 4/1995 |
| JP | 7-120398 | 5/1995 |
| JP | 7-146241 | 6/1995 |
| JP | 7-174704 | 7/1995 |
| JP | 7-253482 | 10/1995 |
| JP | 7-270393 | 10/1995 |
| JP | 8-92511 | 4/1996 |
| JP | 9-292384 | 11/1997 |
| JP | 10-17814 | 1/1998 |
| JP | 10-30986 | 2/1998 |
| JP | 10-253541 | 9/1998 |
| JP | 10-267852 | 10/1998 |
| JP | 2000-105230 | 4/2000 |
| JP | 2002-350419 | 12/2002 |
| JP | 2003-130863 | 5/2003 |
| WO | 2005/053821 | 6/2005 |

OTHER PUBLICATIONS

Machine Translation of JP 2000-105230.*
Machine Translation of KR 10-2006-0111645.*
Translation of JP 58-216936.*
Human Translation of JP 58-216936 published on Dec. 16, 1983.*
Search report from E.P.O. that issued with respect to patent family member European Patent Application No. 07742374.7, mail date is Mar. 31, 2011.
Singapore Office action that issued with respect to patent family member Singapore Patent Application No. 200807576-4, mail date is Oct. 31, 2009.
China Office action that issued with respect to patent family member Chinese Patent Application No. 2007800147644, mail date is Jan. 8, 2010.

* cited by examiner

*Primary Examiner* — Gerard Higgins
*Assistant Examiner* — Sathavaram I Reddy
(74) *Attorney, Agent, or Firm* — Greenblum & Bernstein, P.L.C.

(57) ABSTRACT

Disclosed is a humidity indicator which contains no heavy metal and has good visibility of a color change that occurs when the humidity is increased. The humidity indicator can be produced by applying an aqueous coating comprising a leuco dye, an acidic compound which is in a solid state at ambient temperature, a deliquescent substance and an aqueous resin emulsion onto a substrate such as a resin film, a nonwoven fabric or a paper, and heating and drying the resulting product.

8 Claims, No Drawings

COATING FOR HUMIDITY INDICATOR, METHOD FOR PRODUCTION OF THE COATING, AND HUMIDITY INDICATOR USING THE COATING

TECHNICAL FIELD

The present invention relates to a humidity indicator which changes colors such that an increase in humidity is visible easily, a coating for the humidity indicator used for production of the humidity indicator and a method for production of the same.

BACKGROUND ART

As a desiccant which is sealed in a commodity package, a silica gel-containing pouch has been used conventionally, and the pouch has therein mixed cobalt chloride-impregnated silica gel which is called blue gel as an indicator used to know a dry state. But, since the cobalt is a heavy metal, a cobalt-free humidity indicator has been desired in terms of environments.

Patent Literature 1 discloses a humidity indicator which is formed of a dry molded body of a mixture of a powdery deliquescent material and a powdery color developer which develops a color by contacting with a deliquescence of the deliquescent material. But, the humidity indicator of Patent Literature 1 has a disadvantage that visibility of a color change is insufficient when humidity is increased because a pH indicator or a water-soluble pigment such as a synthetic colorant is used as a color developer.

Besides, various types of humidity indicators such as a sheet type are being demanded, and the above dry molded body cannot comply with the demands at present.
Patent Literature 1: JP-A No. Hei 7-174704

SUMMARY OF THE INVENTION

Problems to be Solved by the Invention

The present invention has been made to overcome the above problems and has an object to provide a humidity indicator which contains no heavy metal, has good visibility of a color change that occurs when the humidity is increased and can be applied to various modes; a coating for the humidity indicator for production of the humidity indicator; and a method for production of the same. Besides, the present invention provides various types of humidity indicators.

Means for Solving the Problems

A first aspect of the present invention is a coating for a humidity indicator, comprising at least an electron donative coloration compound, an acidic compound which is in a solid state at ambient temperature, a deliquescent substance, and an aqueous resin emulsion.

The coating for a humidity indicator of the present invention preferably further contains an organic solvent, and a second aspect of the present invention is a method for production of the coating for a humidity indicator of the present invention containing the organic solvent, comprising finely dispersing and/or dissolving at least an electron donative coloration compound, an acidic compound which is in a solid state at ambient temperature and a deliquescent substance into an aqueous resin emulsion, and adding an organic solvent.

A third aspect of the present invention is a coating for a humidity indicator, comprising at least an electron donative coloration compound, an acidic compound which is in a solid state at ambient temperature, a deliquescent substance and an aqueous solution of a water-soluble polymer compound.

The coating for a humidity indicator of the third aspect of the present invention preferably further contains an organic solvent, and a fourth aspect of the present invention is a method for production of the coating for a humidity indicator of the present invention containing the organic solvent, comprising finely dispersing and/or dissolving at least an electron donative coloration compound, an acidic compound which is in a solid state at ambient temperature and a deliquescent substance into an aqueous solution of a water-soluble polymer compound, and adding an organic solvent.

A fifth aspect of the present invention is a humidity indicator which has a coloration composition supported on a substrate, wherein the coloration composition comprises at least an electron donative coloration compound, an acidic compound which is in a solid state at ambient temperature, a deliquescent substance and a resin binder, and the coating for a humidity indicator of the present invention is adhered to the substrate and heated to dry.

The humidity indicator of the present invention includes as preferable aspects that a chromatic color ink layer is provided between the substrate and the coloration composition, the heated and dried coloration composition has a color different from the chromatic color ink layer, and the surface is at least partially covered with a speed adjustment resin layer.

Effects of the Invention

The present invention provides the following effects.

[1] The coating for a humidity indicator of the present invention is an aqueous coating and therefore can be handled easily.

[2] The humidity indicator of the present invention can be obtained easily by adhering an aqueous coating to a substrate such as paper, a resin film, cloth, a nonwoven fabric or the like and drying. Thus, various types of humidity indicators can be provided and used for wide uses.

[3] Since the humidity indicator of the present invention uses an electron donative coloration compound, a color change indicating that humidity has increased is finely visible, the color can be restored by heating, and reuse is possible. Colors at the time of drying and moistening can be selected as desired, and a humidity level can also be detected according to the color change. Besides, a discoloration rate can also be adjusted easily and can be adjusted according to usage and the production process.

[4] Since the humidity indicator and the coating for a humidity indicator of the present invention do not contain a heavy metal such as cobalt, they are free from environmental problems and can be discarded in the same manner as general household garbage.

[5] Since the humidity indicator of the present invention can also be used as a packaging material, a separate labor of housing the humidity indicator can be omitted by using as the packaging material for a package requiring the interior kept in a dry state or as a packaging material for a desiccant to be housed within a package, and there is no possibility of omitting the addition of the humidity indicator.

BEST MODE FOR CARRYING OUT THE INVENTION

Details of the present invention are described below in detail.

A humidity indicator of the present invention is comprised of supporting a coloration composition on a substrate and produced by adhering an aqueous coating containing a prescribed component to the substrate and heating to dry.

The substrate used in the present invention can be formed of any material if the coloration composition which contains the component of the coating can be supported on the surface and interior of the substrate by adhering the aqueous coating to paper, a resin film, cloth, a nonwoven fabric or the like and heating to dry. As the resin film, a film or a sheet of polyethylene terephthalate (PET), polypropylene (PP), polyethylene (PE) or the like is used preferably.

The coloration composition according to the present invention comprises at least an electron donative coloration compound, an acidic compound which is in a solid state at ambient temperature, a deliquescent substance and a resin binder.

The electron donative coloration compound is not limited to a particular one if it is a compound which is caused to develop a color with an acid, but specifically, a leuco dye is used preferably. For example, a pH indicator, a triarylmethane derivative, a fluoran derivative or the like which develops a color or causes a color change if acidified is used. Specifically, examples are crystal violet lactone, 3-indolino-3-p-dimethylaminophenyl-6-dimethylaminophthalide, 3-diethylamino-7-chlorofluoran, 2-(2-fluorophenylamino)-6-diethylaminofluoran, 2-(2-fluorophenylamino)-6-di-n-butylaminofluoran, 3-diethylamino-7-cyclohexylaminofluoran, 3-diethylamino-5-methyl-7-tert-butylfluoran, 3-diethylamino-6-methyl-7-anilinofluoran, 3-diethylamino-6-methyl-7-p-butylanilinofluoran, 3-cyclohexylamino-6-chlorofluoran, 2-anilino-3-methyl-6-(N-ethyl-p-toluidino)-fluoran, 3-pyrrolidino-6-methyl-7-anilinofluoran, 3-pyrrolidino-7-cyclohexylaminofluoran, 3-N-methylcyclohexylamino-6-methyl-7-anilinofluoran, 3-N-ethylpentylamino-6-methyl-7-anilinofluoran, etc.

The acidic compound is not limited to a particular one if it is in a solid state at ambient temperature, but its examples include oxalic acid, malonic acid, citric acid, salicylic acid, benzoic acid, boric acid, p-toluenesulfonic acid and the like. Among them, oxalic acid, malonic acid and p-toluenesulfonic acid are desirable in terms of a high solubility in water.

The deliquescent substance is not limited to a particular one if it is a substance having deliquescence, but it is preferably salts, and more preferably metallic salts. Examples of the deliquescent substance are magnesium chloride, sodium chloride, potassium chloride, calcium chloride, strontium chloride, barium chloride, magnesium nitrate, calcium nitrate, strontium nitrate, barium nitrate, magnesium bromide, and the like. Among them, it is desirable to use a substance with deliquescence having little temperature dependence, because stable humidity indicating capability can be exerted regardless of a change in temperatures. Examples of the substance deliquescence having little temperature dependence include magnesium chloride, sodium chloride, potassium chloride, and the like.

A mixing ratio of a deliquescent substance (as hydrate) and an acidic compound in the coating of the present invention is preferably in a weight ratio of 200:1 to 1:5, and more preferably 100:1 to 1:2. And, a content of an electron donative coloration compound in the coating is preferably 0.05 to 20.0 wt. %, and more preferably 0.1 to 10.0 wt. %.

In the present invention, the above-described electron donative coloration compound, acidic compound and deliquescent substance are charged into an aqueous resin emulsion or an aqueous solution of a water-soluble polymer compound and stirred thoroughly to finely disperse and/or dissolve, thereby providing a coating for a humidity indicator.

The resin emulsion is not limited to a particular one if it is an aqueous emulsion which is solidified to become a resin binder to support the above-described component by heating to dry at a level of not affecting on the substrate, does not react with a deliquescent substance or an acidic compound, and is not aggregated by the presence of the above components. And, a nonion emulsion is used preferably, and specifically an acrylic emulsion is used preferably. In addition, a weak anion emulsion or the like can be used preferably. The resin emulsion can be used appropriately in a state diluted with water, and a level of color development of the humidity indicator can be adjusted by appropriately selecting an emulsion concentration.

As the water-soluble polymer compound, polyvinyl alcohol (PVA), polyvinylpyrrolidone (PVP) or hydroxyethyl cellulose (HEC) is used preferably, and preferably used as an aqueous solution of 1 to 20 wt. %. In a case where a water-soluble polymer compound such as polyvinyl alcohol is used, the water-soluble polymer compound elutes when a coloration composition absorbs moisture, and the coated surface might become somewhat sticky. Thus, the aqueous resin emulsion is used preferably in the present invention.

Especially, when the aqueous resin emulsion is used, the deliquescent substance is supplied in a state homogeneously dissolved in an aqueous solvent of the resin emulsion, so that the deliquescent substance is dispersed at a molecular level into the resin binder and also present in a fine and uniform state in the coloration composition. Therefore, the deliquescent substance is also deliquesced by a very small volume of moisture which is in contact with the coloration composition to enable to discolor the electron donative coloration compound. Besides, the coloration composition itself is easy to absorb moisture because the resin emulsion is used.

Since a solid acidic compound can be finely dispersed and/or dissolved homogeneously into an aqueous solvent such as an aqueous resin emulsion or an aqueous solution of a water-soluble polymer compound, the electron donative coloration compound can be made to uniformly and finely develop a color in the coating.

Thus, the coloration composition of the humidity indicator of the present invention can detect moisture in the air very sensitively.

By selecting an acidic compound having a high solubility in water or by enhancing dispersibility of the electron donative coloration compound into the coating, these components are finely dispersed into the resin binder, so that the physical strength of the resin binder can be enhanced, and the coloration composition can be made hard to separate from the substrate.

The present invention includes as a preferable embodiment a configuration that an organic solvent is added to the above-described coating for a humidity indicator. As the organic solvent, a polar solvent which has a solubility in water of 5 ml/100 ml or more and is vaporized by heating is used preferably. Specifically, one kind among methanol, ethanol, 1-propanol, 2-propanol, 1-butanol, 2-butanol, 2-methyl-1-propanol, tert-butyl alcohol, methyl ethyl ketone, ethyl acetate, tetrahydrofuran, cyclohexanone, acetone, acetonitrile or a mixture solvent containing at least one of them is used preferably.

The organic solvent is added after the above-described electron donative coloration compound, deliquescent substance and acidic compound are finely dispersed and/or dissolved into an aqueous resin emulsion or an aqueous solution of a water-soluble polymer compound. In other words, before the organic solvent is added, the electron donative coloration compound, deliquescent substance and acidic compound are finely dispersed and/or dissolved into the aqueous resin emulsion or the aqueous solution of the water-soluble polymer compound, so that the individual components can be finely dispersed and/or dissolved homogeneously into the coating as described above. The added amount of the organic solvent is preferably 10 to 100 parts by volume to a total of 100 parts by volume of the above-described electron donative coloration compound, deliquescent substance, acidic compound, aqueous resin emulsion or an aqueous solution of the water-soluble polymer compound.

To the above-described coating may be added an antifoam agent and an antiseptic agent in a range not deteriorating the effects of the present invention, if necessary.

According to the present invention, the above-described coating for the humidity indicator is adhered to the substrate and heated to dry to obtain the humidity indicator which has the coloration composition, which is formed of the electron donative coloration compound, the deliquescent substance, the acidic compound and the resin binder derived from the resin emulsion or the water-soluble polymer compound contained in the coating, supported on the substrate. The method of adhering the coating to the substrate is not limited to a particular one if a desired amount of the coating can be adhered to the substrate, and it is appropriately selected from, for example, a method of immersing the substrate in the coating, a method of coating with a wire bar, a roll coater or the like, a method of spraying by a spray nozzle or the like depending on the compositions of the substrate and the coating.

As the heating method, an oven or the like can be used appropriately. A heating temperature and a heating time are preferably 40 to 150 degrees C., more preferably 50 to 130 degrees C. and preferably 2 to 600 seconds though variable depending on the material of the substrate and the coating composition. It is also possible to support a prescribed amount of the coloration composition by repeating the adhesion of the coating and the heating to dry plural times. For example, when the substrate is a flat one such as a film, the amount of the coloration composition supported by the dried humidity indicator is preferably 0.3 to 100 $g/m^2$.

Since the humidity indicator of the present invention can be obtained by adhering an aqueous coating to the substrate such as paper, a film or the like, a desired size of indicator can be mass produced readily by supporting the coloration composition on the substrate having a large area and cutting it.

The humidity indicator of the present invention obtained as described above indicates an increase in humidity by discoloring (including decoloration) the deliquescent substance contained in the coloration composition supported by the substrate is deliquesced by moisture, and the resultant water content acts on the electron donative coloration compound. The coloration composition which is discolored once can be restored easily to have the color before the discoloring by heating in an oven or the like.

The humidity indicator of the present invention can be used in a state that the coloration composition is supported on the substrate and can be used as it is for various types of uses requiring the humidity control. And, the following various types of embodiments can be adopted preferably. The following embodiments may be performed independently or in combination of plural embodiments.

[Speed Adjustment Resin Layer]

The coloration composition according to the present invention might discolor before packaging into a package if the discoloration rate is fast because it sharply detects an increase in humidity and discolors. Therefore, it is desirable to delay the discoloration rate by limiting moisture which is contacted to the coloration composition by covering the exterior with the speed adjustment resin layer depending on the used coloration composition.

As such a speed adjustment resin layer, a transparent resin layer having appropriate moisture permeability may be used, and it is formed by coating a resin coating, which has a resin material dissolved or dispersed into a solvent, on a substrate which has supported the coloration composition and heating to dry, and laminating a resin sheet or film on the substrate by lamination or the like.

Such a resin material may be any type if it exhibits appropriate moisture permeability and transparency after the resin layer is formed. The moisture permeability of the speed adjustment resin layer according to the present invention is indicated by moisture permeability ($g/m^2$·day) according to the following measuring method.

A measuring resin layer is formed on a PET film having a thickness of 12 μm and measured by a water vapor transmission rate testing system ("PERMATRAN-W 3/33 series" manufactured by MOCON).

The moisture permeability of the speed adjustment resin layer is not particularly limited if a speed adjusting action can be obtained, but it is preferably 0.5 to 200 $g/m^2$·day. If the moisture permeability is less than 0.5 $g/m^2$·day, the moisture permeability is excessively low, so that the discoloration rate becomes excessively slow even if moisture is detected. If it exceeds 200 $g/m^2$·day, the moisture permeability is excessively high, and there is a possibility of a sharp change due to ambient moisture in the packing work or the like.

Specifically, as the resin material, polyethylene terephthalate, butyral resin, polyester-urethane, polyamide, polyvinylidene chloride, styrenated epoxy resin, epoxy resin, phenoxy resin, polyester resin, vinyl chloride acetate, acrylic resin, nitrocellulose and the like can be used.

[Chromatic Color Ink Layer]

As a mode of more clearly detecting an increase in humidity by the humidity indicator of the present invention, there is a configuration that a chromatic color ink layer having a color different from that of the heated and dried coloration composition is previously formed on a substrate by using a coloration composition which is decolored by moistening. For example, in a case where the coloration composition is blue before it is moistened, a red ink is applied onto the substrate, and the ink layer is covered with the coloration composition. Then, a blue color of the coloration composition is visible when drying, and the coloration composition is decolored due to an increase in humidity, so that a red ink layer having been covered with the coloration composition becomes visible. Namely, the humidity indicator changes from the blue color to the red color because of the increase in humidity, so that an increase in humidity is detected at first sight. And, the ink layer can be detected more clearly by printing a prescribed design or letters.

In a case where the substrate is a transparent material, the ink layer may be provided on the side opposite to the surface on which the coloration composition is coated.

The same effect can also be obtained by using a substrate, which is colored to have a prescribed color, instead of the above ink layer.

[Packaging Material 1]

In a case where a package such as foods, electronic parts or the like is kept in a dry state by housing a desiccant in the package, the humidity indicator of the present invention can be applied to the packaging material of the desiccant.

Specifically, a material having moisture permeability is used as the substrate, and the coloration composition of the present invention is supported on the substrate to use as the packaging material of the desiccant.

In the above structure, since a material having moisture permeability is used as the substrate, the coloration composition is supported outside of the substrate if the substrate is not transparent, and the coloration composition may be supported either outside or inside the substrate if the substrate is transparent. As the substrate, one which has plural holes having a diameter smaller than the desiccant formed in the resin sheet is also used preferably other than a material having moisture permeability such as a nonwoven fabric.

For example, the coloration composition is supported by applying the coating for a humidity indicator of the present invention to the exterior of a nonwoven fabric and heating to dry. Then, the coloration composition is covered with a speed adjustment resin layer. And, a transparent resin sheet having low moisture permeability or substantially not having it is provided with plural holes having a diameter smaller than the desiccant, and the coloration composition is supported on a region not provided with the holes. In addition, as the coloration composition, one which is decolored with moistening is used, and a chromatic color ink layer having a color different from the coloration composition is provided on the inner side of the coloration composition, so that an increase in humidity can be detected better.

According to such an embodiment, since the desiccant and the humidity indicator are not required to be housed separately into the package, a packing work becomes simple, and the humidity indicator can be prevented from not being added.

[Packaging Material 2]

By appropriately selecting the substrate and the speed adjustment resin layer, the humidity indicator of the present invention can be used as it is as the packaging material of a package such as foods, electronic parts or the like requiring retention of a dry package interior.

Specifically, it is configured to decrease the moisture permeability outside the coloration composition and preferably to substantially eliminate the moisture permeability, and to have appropriate moisture permeability in the inside. Here, the outside means the package outside, and the inside means the package interior (the side accommodating a packed article).

More specifically, there is preferably used a structure that a coated surface is formed by using as the substrate a material having low moisture permeability or substantially not having it and using the coating for the humidity indicator of the present invention for the inside, or covering the coated surface of the structure with the speed adjustment resin layer.

In the above structure, the substrate has preferably a moisture permeability of 1 $g/m^2 \cdot day$ or less, and the speed adjustment resin layer is preferably configured to have a moisture permeability of 10 $g/m^2 \cdot day$ or more. If the substrate has a moisture permeability of exceeding 1 $g/m^2 \cdot day$, it tends to be affected by outside humidity, and even when the humidity in the package is not increased, discoloring may be caused if the outside humidity increases. If the speed adjustment resin layer has a moisture permeability of less than 10 $g/m^2 \cdot day$, an increase in humidity within the package might not be reflected satisfactorily.

In a case where the coloration composition of the humidity indicator is very sensitive to an increase in humidity, there is a possibility that discoloring is caused by sharp reaction to ambient humidity in the packing work. Thus, it is preferable that the speed adjustment resin layer is determined to have a moisture permeability of 200 $g/m^2 \cdot day$ or less.

It is necessary that the above substrate is transparent to a level such that discoloring of the coated surface of the coloration composition due to an increase in humidity can be recognized from outside. And, for the substrate, an alumina-deposited layer or a silica-deposited layer according to prior art such as CVD, PVD is preferably provided to keep the package interior in the dry state. By provision of the deposited layer, the moisture permeability can be determined to be 1 $g/m^2 \cdot day$ or less.

Besides, to improve the adhesiveness of the coated surface of the coloration composition, an anchor coat layer may be formed on one or both sides of the coated surface. As the anchor coat layer, a known one is used, and preferably vinyl chloride-vinyl acetate copolymer, urethane resin or the like is used.

For the packaging material, a coloration composition which is decolored by moistening is used, and a chromatic color ink layer having a color different from the coloration composition is provided on the inner side of the coloration composition, so that an increase in humidity can be detected better.

[Printing]

The present invention preferably uses cloth, a nonwoven fabric or paper as the substrate. As described above, the resin film and the like can also be used as the substrate, but the resin film has moisture permeability lower than the substrate formed of fiber. Therefore, a humidity indicator which is formed by applying the coating for a humidity indicator of the present invention onto the resin film is easy to absorb moisture on the coating-applied surface, but moisture absorption on the side opposite to the coated surface is inferior, and if the coated surface comes into contact with a packaging material or the like, it becomes hard that the coloration composition is moistened, and it becomes hard to detect an increase in humidity. Such a problem can be eliminated by forming the coated surface on both sides of the resin film, but the process of applying the coating and heating to dry must be repeated two times, so that the production processes become troublesome.

The substrate formed of fiber is easy to adhere because the coating for a humidity indicator of the present invention soaks, so that the coloration composition can be supported on both sides of the substrate in a single process of coating and heating to dry.

But, in a case where a prescribed pattern such as letters, designs or the like is printed on the substrate formed of fiber, blotting is induced, so that it is inferior in reproducibility of color tone, fine dots and the like. Therefore, when the substrate formed of fiber is used, a resin film is laminated on at least one side of the substrate to solve the above problem. In other words, the humidity indicator can be provided with clear printing with good reproducibility by previously printing on the resin film suitable for printing and laminating on the substrate.

But, in comparison with the substrate formed of fiber, the resin film has lower moisture permeability, and when the substrate is covered with the resin film, the coloration composition supported by the substrate is hardly contacted to moisture. Therefore, the area covered with the resin film in this structure is determined to be a part of the substrate so as to secure the exposed surface of the substrate.

In a case where the pertinent resin film is laminated on only one side of the substrate, the resin film partially covers the one side, while the other side exposes the substrate on the whole surface. When the resin film is laminated on both sides of the substrate, it is configured to mutually overlap the exposed surfaces on the both sides of the substrate.

By configuring as described above, the humidity indicator of the present invention has inevitably the area with both sides exposed within the substrate and can easily absorb moisture from both sides of the substrate at the pertinent area. Thus, even if one exposed side is in a state of hardly absorbing moisture in contact with the packaging material of the package in which the humidity indicator is housed, an increase in humidity by absorbing moisture by the other exposed side can be detected.

In a case where the resin film is laminated on both sides of the substrate, there may be formed an area that both sides of the substrate are covered with the resin film, but even if humidity increases on the pertinent area, the coloration composition is hardly moistened, and the discoloration rate is apparently delayed in comparison with the exposed side. Therefore, it becomes easy to detect discoloring on the exposed side by comparing them when humidity is increased.

As the resin film to be laminated on the substrate, the material of the speed adjustment resin layer described above can be used. For example, a film of polyethylene terephthalate (PET), polypropylene (PP), polyethylene (PE) or the like is preferably used, but the PET film suitable for printing is more preferable.

For the humidity indicator of this configuration, one which is decolored by moistening is used as the coloration composition, and the substrate is provided with a chromatic color ink layer having a color different from the coloration composition at the time of drying before the coating is adhered to the substrate. Thus, an increase in humidity can be detected more easily.

EXAMPLES

Example 1

One part by weight of a leuco dye "BLUE-63" (manufactured by Yamamoto Chemicals Inc.), 1 part by weight of oxalic acid dihydrate (manufactured by Wako Pure Chemical Industries, Ltd.) and 10 parts by weight of magnesium chloride hexahydrate were added to 100 parts by weight of acrylic emulsion "DICNAL RS-308" (solid component of 40 wt. %, manufactured by Dainippon Ink and Chemicals), and they were stirred so as to become homogeneous. The obtained coating was applied onto a PET film using #20 wire bar such that the dried coloration composition amount became 16 g/m$^2$ and dried at 80 degrees C. for one minute to obtain a humidity indicator.

Example 2

A humidity indicator was obtained by the same manner as in Example 1 except that 6 parts by weight of oxalic acid dehydrate and 20 parts by weight of magnesium chloride hexahydrate were used.

Example 3

A humidity indicator was obtained by the same manner as in Example 1 except that 10 parts by weight of calcium chloride dihydrate was used instead of the magnesium chloride hexahydrate.

Example 4

A humidity indicator was obtained by the same manner as in Example 1 except that 6 parts by weight of oxalic acid dehydrate was used and 20 parts by weight of calcium chloride dihydrate was used instead of the magnesium chloride hexahydrate.

Example 5

One part by weight of a leuco dye "RED-40" (manufactured by Yamamoto Chemicals Inc.), 1 part by weight of oxalic acid dihydrate and 10 parts by weight of magnesium chloride hexahydrate were added to 100 parts by weight of acrylic emulsion "DICNAL E-8203WH" (solid component of 45 wt. %, manufactured by Dainippon Ink and Chemicals), and they were stirred so as to become homogeneous. The obtained coating was applied onto a PET film using #14 wire bar such that the dried coloration composition amount became 15 g/m$^2$ and dried at 80 degrees C. for one minute to obtain a humidity indicator.

Example 6

One-half part by weight of a leuco dye "BLUE-63", 0.1 part by weight of oxalic acid dihydrate and 10 parts by weight of magnesium chloride hexahydrate were added to 100 parts by weight of acrylic emulsion "DICNAL E-8203WH", and they were stirred so as to become homogeneous. The obtained coating was applied onto a PET film using #20 wire bar such that the dried coloration composition amount became 16 g/m$^2$ and dried at 80 degrees C. for one minute to obtain a humidity indicator.

Example 7

A humidity indicator was obtained by the same manner as in Example 6 except that 10 parts by weight of oxalic acid dehydrate was used.

Example 8

A humidity indicator was obtained by the same manner as in Example 6 except that 0.1 part by weight of a leuco dye "BLUE-63", 1 part by weight of oxalic acid dihydrate, and 9 parts by weight of magnesium chloride hexahydrate were used.

Example 9

A humidity indicator was obtained by the same manner as in Example 6 except that 20 parts by weight of a leuco dye "BLUE-63", 1 part by weight of oxalic acid dihydrate, and 9 parts by weight of magnesium chloride hexahydrate were used.

Example 10

A humidity indicator was obtained by the same manner as in Example 6 except that 1 part by weight of a leuco dye "BLUE-63" and 1 part by weight of malonic acid instead of oxalic acid dehydrate were used.

(Evaluation)

The humidity indicators obtained in Examples 1 to 10 were left standing under environments of 8% RH, 20% RH, 50% RH and 90% RH for 24 hours to observe color changes. And, the indicators left standing under the environment of 90% RH was dried in an oven at 80 degrees C. for ten minutes, and the color changes were observed. The results are shown in Table 1.

TABLE 1

|  |  | Example 1 | Example 2 | Example 3 | Example 4 | Example 5 |
|---|---|---|---|---|---|---|
| Leuco dye | BLUE-63 | 1 part by weight | 1 part by weight | 1 part by weight | 1 part by weight | — |
|  | RED-40 | — | — | — | — | 1 part by weight |
| Acid compound | Oxalic acid dihydrate | 1 part by weight | 6 parts by weight | 1 part by weight | 6 parts by weight | 1 part by weight |
|  | Malonic acid | — | — | — | — | — |

TABLE 1-continued

| Deliquescent substance | MgCl₂•6H₂O | 10 parts by weight | 20 parts by weight | — | — | 10 parts by weight |
|---|---|---|---|---|---|---|
| | CaCl₂•2H₂O | — | — | 10 parts by weight | 20 parts by weight | — |
| Emulsion | DICNAL RS-308 | 100 parts by weight | 100 parts by weight | 100 parts by weight | 100 parts by weight | — |
| | DICNAL E-8203WH | — | — | — | — | 100 parts by weight |
| Evaluation | 8% RH | Blue | Blue | Blue | Green | Red |
| | 20% RH | Light purple | Light purple | Colorless | Light purple | Colorless |
| | 50% RH | Colorless | Light purple | Colorless | Light purple | Colorless |
| | 90% RH | Colorless | Colorless | Colorless | Colorless | Colorless |
| | 90% RH→80° C. × 10 min | Blue | Blue | Light blue | Light blue | Red |

| | | Example 6 | Example 7 | Example 8 | Example 9 | Example 10 |
|---|---|---|---|---|---|---|
| Leuco dye | BLUE-63 | 0.5 part by weight | 0.5 part by weight | 0.1 part by weight | 20 parts by weight | 1 part by weight |
| | RED-40 | — | — | — | — | — |
| Acid compound | Oxalic acid dihydrate | 0.1 part by weight | 10 parts by weight | 1 part by weight | 1 part by weight | — |
| | Malonic acid | — | — | — | — | 1 part by weight |
| Deliquescent substance | MgCl₂•6H₂O | 10 parts by weight | 10 parts by weight | 9 parts by weight | 9 parts by weight | 10 parts by weight |
| | CaCl₂•2H₂O | — | — | — | — | — |
| Emulsion | DICNAL RS-308 | — | — | — | — | — |
| | DICNAL E-8203WH | 100 parts by weight | 100 parts by weight | 100 parts by weight | 100 parts by weight | 100 parts by weight |
| Evaluation | 8% RH | Light blue | Blue | Light blue | Blue | Light blue |
| | 20% RH | Colorless | Light blue | Colorless | Blue | Colorless |
| | 50% RH | Colorless | Light blue | Colorless | Blue | Colorless |
| | 90% RH | Colorless | Light blue | Colorless | Light blue | Colorless |
| | 90% RH→80° C. × 10 min | Light blue | Blue | Light blue | Blue | Light blue |

Examples 11 to 13

One part by weight of a leuco dye "BLUE-63" (manufactured by Yamamoto Chemicals Inc.), 1 part by weight of oxalic acid dihydrate (manufactured by Wako Pure Chemical Industries, Ltd.) and 10 parts by weight of magnesium bromide hexahydrate (manufactured by Wako Pure Chemical Industries, Ltd.) were added to a mixture solution of 80 parts by weight of acrylic emulsion "DICNAL E-8203WH" (solid component of 45 wt. %, manufactured by Dainippon Ink and Chemicals) and 40 parts by weight of 2-propanol, and they were stirred so as to become homogeneous. The obtained coating was applied onto the surface of a nonwoven fabric ("Tyvek 1082D" manufactured by Du Pont Kabushiki Kaisha) using #20 wire bar such that the dried coloration composition amount became 8 g/m², and dried at 80 degrees C. for one minute to support a blue coloration composition on the nonwoven fabric.

Then, PET films (ester film "E5100" manufactured by Toyobo Co., Ltd.) having 12 μm, 25 μm and 50 μm in thickness were dry laminated on both sides of the nonwoven fabric described above to form a speed adjustment resin layer on the surface.

Examples 14 to 27

The coating used in Example 11 was applied onto a surface of a PET film ("COSMOSHINE A4300" manufactured by Toyobo Co., Ltd.) having a thickness of 100 μm using #20 wire bar such that the dried coloration composition amount became 8 g/m² and dried at 80 degrees C. for one minute to support a blue coloration composition.

Then, coatings containing the resin components shown in Table 3 each were applied in the coated amount (solid content after drying) shown in Table 3 on both sides using #20 wire bar and dried at 80 degrees C. for one minute to form speed adjustment resin layers.

(Evaluation)

The individual humidity indicators of Examples 11 to 27 were left still under environments of ambient temperature, normal pressure and 50% RH, color changes were observed visually, and time in which a color had faded completely was measured. The results are shown in Table 2 (Examples 11 to 13) and Table 3 (Examples 14 to 27).

It is apparent from Tables 2 and 3 that the provision of the speed adjustment resin layer makes it possible to adjust a discoloration rate of the humidity indicator. Especially, the humidity indicator provided with the speed adjustment resin layer formed of polyvinylidene chloride took 1800 seconds before it is decolored with moisture in the air under the above described evaluation conditions. According to the present invention, therefore, there is no possibility of causing a difference in discoloring level which can be checked visually on every package depending on a difference in exposure time even when the humidity indicator was exposed to the air in an ordinary packaging work of electronic parts or the like.

TABLE 2

| | Speed adjustment resin layer | | | |
|---|---|---|---|---|
| | Resin | Thickness (μm) | Moisture permeability (g/m² · day) | Discoloration time(s) |
| Example 11 | PET | 12 | 39.02 | 600 |
| Example 12 | PET | 25 | 20.59 | 1200 |
| Example 13 | PET | 50 | 10.06 | 2700 |

TABLE 3

| | Speed adjustment resin layer | | | | | |
|---|---|---|---|---|---|---|
| | Coating | | | | Moisture | |
| | Resin | Solvent | Solid content (wt. %) | Coated amount (g/m$^2$) | permeability (g/m$^2$ · day) | Discoloration time (s) |
| Example 14 | Butyral resin | MEK[X.1]/toluene | 10 | 1.04 | 36.07 | 15 |
| Example 15 | Butyral resin | MEK/toluene | 20 | 1.96 | 39.93 | 25 |
| Example 16 | Polyester-urethane | MEK/toluene | 20 | 2.16 | 32.72 | 90 |
| Example 17 | Polyester-urethane | MEK/toluene | 20 | 1.61 | 31.33 | 40 |
| Example 18 | Polyamide | Toluene/IPA | 20 | 1.83 | 37.22 | 39 |
| Example 19 | Polyvinylidene chloride | MEK/toluene | 20 | 3.03 | 4.88 | 1800 |
| Example 20 | Styrenated epoxy resin | MEK/toluene/xylene | 20 | 2.10 | 37.13 | 90 |
| Example 21 | Epoxy resin | MEK/toluene | 20 | 2.31 | 33.98 | 120 |
| Example 22 | Phenoxy resin | MEK/toluene | 20 | 2.58 | 36.38 | 40 |
| Example 23 | Polyester | MEK/toluene | 20 | 2.25 | 34.94 | 55 |
| Example 24 | Polyester | MEK/toluene | 20 | 2.07 | 35.42 | 50 |
| Example 25 | Polyvinyl chloride acetate | MEK/toluene | 15 | 1.46 | 35.78 | 30 |
| Example 26 | Acrylic resin | MEK/toluene | 20 | 1.42 | 39.40 | 20 |
| Example 27 | Nitrocellulose | Ethyl acetate/IPA | 17.5 | 1.63 | 35.50 | 60 |

[X.1]MEK: Methyl ethyl ketone

The invention claimed is:

1. A humidity indicator comprising:
   a substrate; and
   a dried coloration composition supported on the substrate, which is configured to provide a humidity indication and which comprises an electron donative coloration compound, an acidic compound that is in a solid state at ambient temperature, a deliquescent substance, and a resin binder,
   wherein the coloration composition is formed by heating a coating adhered to the substrate to dry the coating, the coating comprising the electron donative coloration compound, the acidic compound that is in a solid state at ambient temperature, the deliquescent substance, an aqueous resin emulsion that is an anionic emulsion, and an organic solvent, and
   wherein the resin binder is derived from drying the anionic aqueous resin emulsion.

2. A humidity indicator according to claim 1, wherein a chromatic color ink layer is provided between the substrate and the coloration composition, and the heated and dried coloration composition has a color different from the chromatic color ink layer.

3. The humidity indicator according to claim 2, wherein a surface is at least partially covered with a speed adjustment resin layer.

4. The humidity indicator according to claim 1, wherein a surface is at least partially covered with a speed adjustment resin layer.

5. A humidity indicator comprising:
   a substrate; and
   a dried coloration composition supported on the substrate, which is configured to provide a humidity indication and which comprises an electron donative coloration compound, an acidic compound that is in a solid state at ambient temperature, a deliquescent substance, and a resin binder,
   wherein the coloration composition is formed by heating a coating adhered to the substrate to dry the coating, the coating comprising the electron donative coloration compound, the acidic compound that is in a solid state at ambient temperature, the deliquescent substance, and an aqueous resin emulsion that is an anionic emulsion, and
   wherein the resin binder is derived from drying the anionic aqueous resin emulsion.

6. The humidity indicator according to claim 5, wherein a chromatic color ink layer is provided between the substrate and the coloration composition, and the heated and dried coloration composition has a color different from the chromatic color ink layer.

7. The humidity indicator according to claim 5, wherein a surface is at least partially covered with a speed adjustment resin layer.

8. The humidity indicator according to claim 6, wherein a surface is at least partially covered with a speed adjustment resin layer.

* * * * *